United States Patent [19]

Vardimon

[11] Patent Number: 4,869,667
[45] Date of Patent: Sep. 26, 1989

[54] HYGIENIC MAGNETIC ERUPTOR

[76] Inventor: Alexander D. Vardimon, 1337 E. Madison Park, Chicago, Ill. 60615

[21] Appl. No.: 50,465

[22] Filed: May 18, 1987

[51] Int. Cl.⁴ ............................................. A61C 7/00
[52] U.S. Cl. ........................................ 433/24; 433/18
[58] Field of Search ........................... 433/18, 173–176, 433/24, 189, 21

[56] References Cited

U.S. PATENT DOCUMENTS

| | | | |
|---|---|---|---|
| 1,215,442 | 2/1917 | Walkers, deceased | 433/21 |
| 3,984,915 | 10/1976 | Noble, deceased et al. | 433/18 |
| 4,017,973 | 4/1977 | Nelson | 433/18 |
| 4,424,030 | 1/1984 | Smiley et al. | 433/18 |
| 4,565,526 | 1/1986 | Kawata et al. | 433/8 |
| 4,595,361 | 6/1986 | Blechman et al. | 433/18 |

FOREIGN PATENT DOCUMENTS

| | | | |
|---|---|---|---|
| 2840370 | 3/1980 | Fed. Rep. of Germany | 433/18 |
| 972790 | 10/1964 | United Kingdom | 433/21 |

*Primary Examiner*—Martin P. Schwadron
*Assistant Examiner*—Allen J. Flanigan
*Attorney, Agent, or Firm*—Jerome Goldberg

[57] ABSTRACT

A hygienic magnetic eruptor compelling and guiding the eruption of an impacted tooth fully embedded inside the jaw, through the gum and into a dental arch space. An intra-magnetic unit may be bonded to the tip of the impacted tooth inside the jaw bone or placed in the bony plate layer between the impacted tooth and the dental arch space. An intra-oral magnetic unit generating a greater magnetic force than the intra-bony magnetic unit is positioned in the dental arch space for pulling the impacted tooth toward the dental arch space. Initially, a surgical procedure is undertaken to provide a flap in the gum at the desired point of entry for accessing the impacted tooth, and thereafter some of the bone which interferes with the normal eruption of the impacted tooth is removed to provide a tunnel to the tip of the crown of the impacted tooth or to the bony plate adjacent to the impacted tooth. A sterile intra-bony magnetic unit is inserted in the tunnel and secured in place and then the flap is reconnected to the gum for aseptically isolating the sterile intra-bony magnetic unit from the non-sterile oral cavity, to almost simulate the natural eruption process of an impacted tooth.

15 Claims, 2 Drawing Sheets

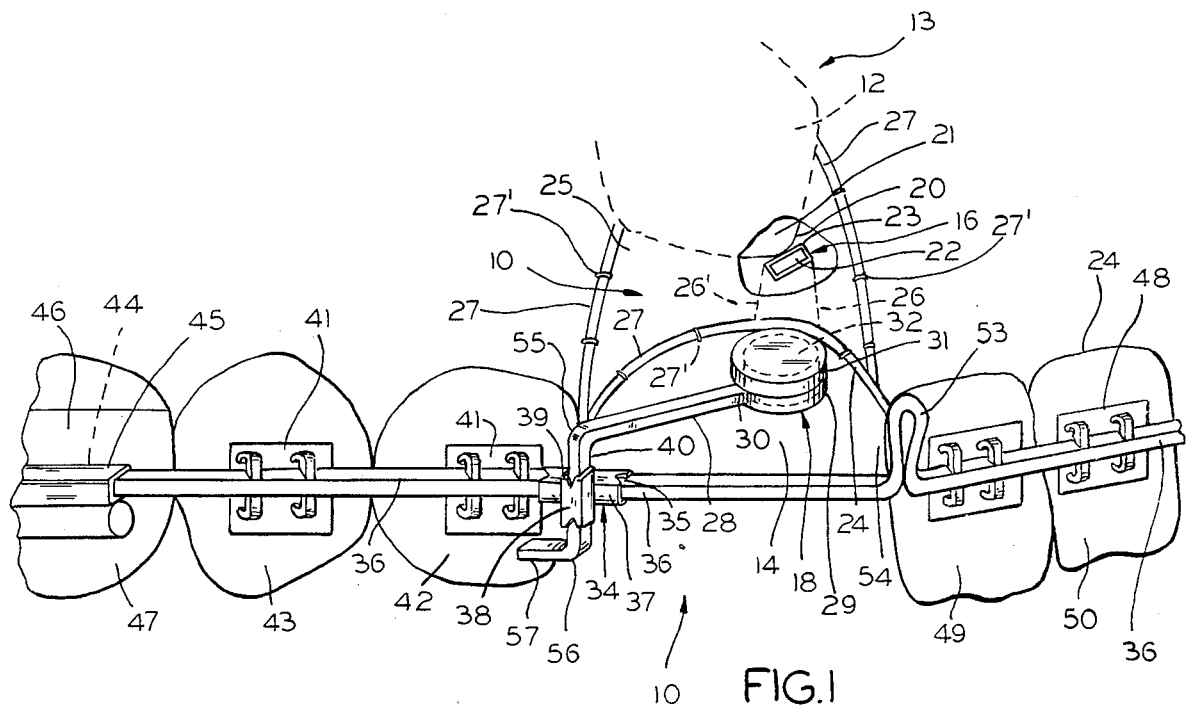
FIG.1
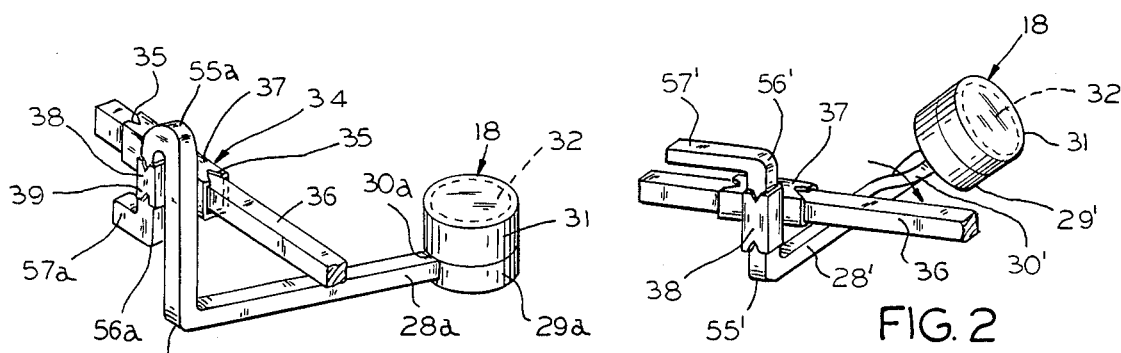
FIG.3    FIG.2
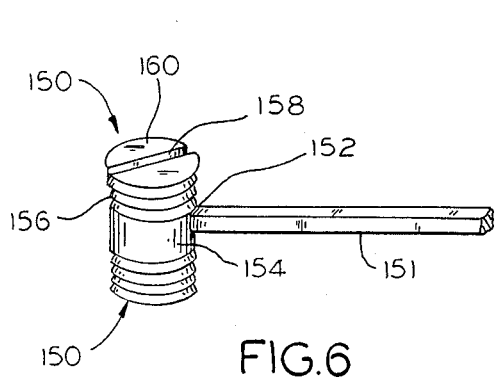
FIG.6
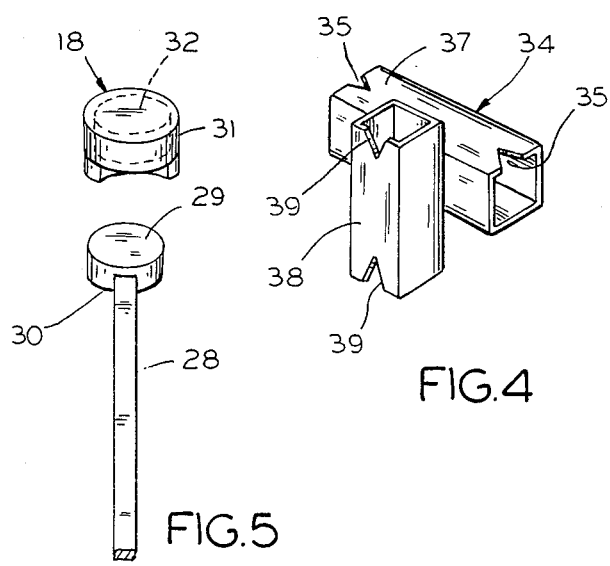
FIG.4
FIG.5

HYGIENIC MAGNETIC ERUPTOR

BACKGROUND OF THE INVENTION

This invention of a hygienic magnetic eruptor relates generally to the field of othodontics, and more specifically relates to the use of magnetic appliances for causing the eruption of impacted teeth.

The conventional approaches applied heretofore for stimulating the eruption of an impacted tooth include: the surgical removal of soft tissue and the bone surrounding the impacted tooth; attaching a force transmitter auxillary to the crown of the impacted tooth by procedures such as cementing a pin, looping a stainless steel wire or bonding a bracket; packing the site with e.g. peridontal pack to prevent healing of the soft tissue over the impacted tooth; and traction with conventional mechanical forces such as rubber bands, coil springs or spring loaded wires.

Some of the deleterious effects which are frequently associated with the conventional techniques for erupting an impacted tooth are dilacerated roots, devitalization, loss of peridontal attachment (pocket), mobility and loss of supporting bone, i.e., recession of the alveolar crest or ridge.

The subject invention overcomes the undesirable effects of the conventional techniques for erupting an impacted tooth by utilizing magnetic appliances for compelling and guiding the path of eruption of an impacted tooth into a dental arch space.

The use of intra-oral magnetic appliances have been disclosed in several patents primarily for correcting misaligned teeth. Representative of these patents are: U.S. Pat. No. 4,565,526, KAWATA ET AL, U.S. Pat. Nos. 4,457,707, 4,424,030, SMILEY ET AL; U.S. Pat. No. 4,396,373, DELLINGER; and U.S. Pat. No. 4,017,973, NELSON.

In my German Pat. No. DE 2840 370 C3, VARDIMON (1982) magnets are also used to align teeth. For a forward extending tooth, magnets are placed in an attractive configuration to pull the tooth backward or in the posterior direction; and conversely, for a backward extending tooth, magnets are placed in a repelling configuration to push the tooth in the forward or anterior direction.

SUMMARY OF THE INVENTION

The hygienic magnetic eruptor is an orthodontic appliance used to stimulate the eruption process of an impacted tooth (or teeth) and to guide the impacted tooth into the dental arch. The hygienic magnetic eruptor includes an intra-bony magnetic unit and an intra-oral magnetic unit, interacting in an attractive force arrangement.

The intra-bony magnetic unit is linked to the impacted tooth in a direct or indirect manner. In the direct linkage the intra-bony magnetic unit is bonded or otherwise attached to the tip of the crown of the impacted tooth. In order to insert the intra-bony magnetic unit into the jaw for attachment to the crown of the impacted tooth, surgical removal is required of the portion of the bony layer covering the tip of the impacted tooth. In the indirect linkage, the intra-bony magnetic unit or a plurality of magnetic particles are inserted into the bony layer adjacent to the impacted tooth.

The intra-oral magnetic unit is located in the dental arch space, often provided in an earlier orthodontic procedure. The magnetic member of the intra-oral magnetic unit is connected to a fixed or removable orthodontic support. The magnetic member is suspended by means of a spatially adjusted lever arm. Vertical adjustments of the lever arm, i.e. changes in the gap between the intra-bony magnet and the intra-oral magnetic member, are made according to the extent of tooth eruption and force requirement. Horizontal adjustments of the lever arm, i.e. altering the amount of overlapping of the two magnets, are made according to mesio-distal and bucco-lingual tooth posture.

The intra-oral magnetic unit can be integrated in the orthodontic appliance of the same dental arch as the impacted tooth or in the opposing jaw. The vertical positioning of the lever arm might require elevation of the bite, and hence an increase in the inter-jaw clearance, particularly in an advanced stage of the treatment when the impacted tooth approaches the occlusal plane.

The hygienic magnetic eruptor of the invention herein improves over the conventional treatment of impacted teeth by operating in virtually at non-inflammatory manner. This is accomplished due to the feasibility of magnetic flux to pass from the intra-bony magnetic unit to the intra-oral magnetic unit through connective tissue and epithlium as an intermediate medium. The non-inflammatory performance of the hygienic magnetic eruptor of this invention is achieved by sealing the oral mucosa (e.g. suturing) after surgical implantation of an intra-bony magnet. Both the intra-bony magnetic unit and the surgical armamentarium are sterilized prior to implantation, to maintain hygienic conditions during and after the surgical procedure. Local and /or systemic antibiotic coverage is indicated.

The material of choice for the intra-bony and intra-oral magnetic unit may be constructed from rare earth magnetic alloys like $SmCo_5$, $Sm_2Co_{17}$ and $Nd_2Fe_{14}B$. The intra-bony magnetic unit can also be made from paramagnetic material like soft iron, especially in the case of indirect linkage in the form of multiple particles. Rare earth intra-bony and intra-oral magnets should be protected against salivary assault by suitable coating. The coating prevents corrosion which causes structural deterioration of the magnetic alloys and consequentially a decay in their magnetic properties. Recommended coating materials are the polymers pol-para-xylylene, methylmetacrylate, teflon and stainless steel.

The characteristic of magnetic force to decline proportional to the second exponential of the distance, enables the attractive force to increase over treatment time. This behavior corresponds to biological safety of tooth movement, whereas an excess in initial traction force can result in devitalization and/or dilaceration of the involved tooth and root(s) respectively.

The hygienic performance of the appliance herein may eliminate the appearance of recession of the alveolar crest and mobility due to loss of periodontal attachment which are common side effects associated with the current ortho-surgical treatment of aligning impacted teeth.

BRIEF DESCRIPTION OF THE DRAWINGS

Referring now to the drawings in which the same characters of reference are employed to indicate corresponding similar parts throughout the several figures of the drawings:

FIG. 1 is a buccal side perspective view of a hygienic magnetic eruptor for pulling and three dimensionally aligning a malposed impacted tooth embedded in the upper jaw into a dental arch space, and showing the intra-bony magnetic unit bonded to the impacted tooth and the intra-oral magnetic unit positioned in the dental arch space, and embodying the principle of the invention;

FIG. 2 illustrates a perspective view of an inclined intra-oral magnetic unit mounted to an arch wire for pulling and three-dimensionally aligning the malposed impacted tooth into the dental arch space after it has partially erupted;

FIG. 3 illustrates a perspective view of a modified version of the intra-oral magnetic unit of FIG. 2, and showing three bends in the lever arm for setting the spatial position of the intra-oral magnetic member for pulling the malposed impacted tooth into the dental arch space;

FIG. 4 illustrates a perspective view of a two dimensional connector having a horizontal sleeve and a vertical tube;

FIG. 5 shows components of the intra-oral magnetic unit of FIGS. 1 and 2 comprising a magnetic member in its housing and a lever arm with a support table;

FIG. 6 illustrates a threaded magnet for use with an alternate embodiment for the intra-oral magnetic unit;

DESCRIPTION OF THE PREFERRED EMBODIMENTS

Figure 7:
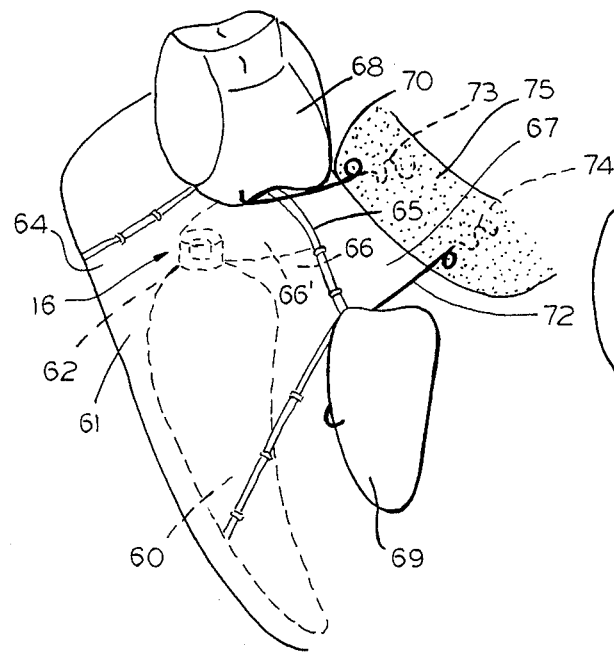
FIG. 7 is a perspective view of a removable hygienic magnetic eruptor prior to placement of the intra-oral magnetic unit and illustrating in phantom an impacted tooth embedded in the lower jaw with the intra-bony magnetic unit bonded to the tip of the tooth, and also showing a pair of spring fingers to form and maintain the dental arch space from a relapse of the adjacent teeth.

Referring now to FIGS. 1 through 5 of the drawings, the reference numeral 10 indicates generally a fixed hygienic magnetic eruptor for compelling and guiding the eruption of an impacted tooth 12 (e.g. upper canine/cuspid in FIG. 1) embedded in the upper jaw 13 into a dental arch space 14. The hygienic magnetic eruptor 10 comprises an intra-osseous (bony) magnetic unit 16 and an intra-oral magnetic unit 18, magnetically attracting to each other.

The intra-bony magnetic unit 16 is bonded to the tip 20 of the crown 21 of the impacted upper cuspid 12 by means of a suitable etching-bonding technique. The intra-bony magnetic unit 16 includes a magnetic piece 22 enclosed by a coating housing 23. The magnetic piece 22 may be constructed from a strong permanent magnetic material such as SmCo5 or a weak magnetic material such as soft iron. The coating housing 23 may be a biocompatible material such as perylene (poly-para xylene), tantalum, stainless steel, teflon, etc. for protecting the magnet 22 from corrosion.

Initially, a surgical procedure is undertaken which usually includes a muco-periosteal incision along the alveolar ridge 24 and also upward if necessary (as viewed in FIG. 1) to provide a buccal flap 25 on the buccal side of the gum. Alternatively, a lingual flap could be formed on the lingual side of the gum (not shown) or flaps on both the buccal and lingual sides of the gum, depending upon the location of the crown 21 of the impacted tooth 12 and the best point for entry into the jaw for accessing the impacted tooth 12.

Upon reflecting or opening the flap 25, a certain amount of bone 26 which interfers with the normal eruption of the impacted tooth 12 is removed, to provide a pathway or tunnel 26' in the jaw 13 to the crown 21 of the impacted tooth 12. A sterile intra-bony magnetic unit 16 is inserted in the tunnel 26' and bonded to the tip 20 of impacted tooth 12. After the intra-bony magnetic unit 16 is bonded in place, the edges 27 of the flap 25 are compressed to the alveolar ridge 12 and coapted together, for example by means of sutures 27', and also reconnected to the gum wherever else the incision was made to form the flap 25. Now the impacted tooth 12 and the intra-bony magnetic unit 16 is aseptically isolated from the non-sterile oral areas, to almost simulate the natural eruption process. A healing period of from 3 to 6 days is required until consolidation of the incision edges 27 is achieved. Thereafter, the intra-oral magnetic unit 18 is positioned in the dental arch space 14 to commence the treatment for pulling the intra-bony magnetic unit 16 and the impacted tooth 12 into the dental arch space 14.

The intra-oral magnetic unit 18 comprises a lever arm 28 (FIGS. 1 and 5) having a flat support table 29 at the outer end 30 thereof to receive a housing 31 containing a magnetic member 32. The arm 28 is spatially rigidly positioned in the dental arch space 14, as will be more fully described below. The housing 31 may be mechanically secured or soldered to the table 29.

The magnetic member 32 of the intra-oral magnetic unit 18 is constructed from a strong paramagnetic material like the rare earth alloys such as SmCo5, Sm3Co17 and Nd2Fe14B, and also has a greater volume than the magnetic piece 22 of the intra-bony magnetic unit 16, to generate a greater magnetic flux density (capable of generating a greater magnetic force) than the magnetic piece 22. The greater magnetic force of the magnetic member 32 and also the fixed position of the lever arm 28 causes a magnetically attractive movement of the intra-bony magnetic unit 18 toward the intra-oral magnetic unit 18, and not vice versa.

A two dimensional connector 34 (FIGS. 1 thru 4) is used for attaching the intra-oral magnetic unit 18 to a main arch wire 36. In FIG. 1, the arch wire 36 extends across the buccal side of the dental arch space 14. The connector 34 includes a crimpable horizontal sleeve 37 secured to a crimpable vertical tube 38. The sleeve 37 and tube 38 include lips 35 and 39 respectively (slotted ends). The arch wire 36 passes through the sleeve 37, and the sleeve 37 is slidable therealong for securing to the arch wire 36 at the distal end 40 of the dental arch space 14.

The arch wire 36 is connected to the dental arch by means of fixed orthodontic appliances such as edgewise premolar brackets 41 bonded to the upper premolar teeth 42 and 43. The posterior end 44 of the arch wire 36 is secured inside a holder member 45 of an edgewise band 46 placed on the upper first molar 47. The arch wire 36 is further supported by edgewise brackets 48 boned to the upper anterior incisor teeth 49, 50.

The horizontal sleeve 37 of connector 34 is affixed to the arch wire 36 by pinching the lips 35 (slotted ends) against the arch wire 36. The attachment of the connector 34 to the arch wire 36 functions as a stop and counteracts any mesial drift of the upper premolar tooth 42 into the dental arch space 14.

The arch wire 36 includes a vertical loop 53 positioned at the mesial end 54 of the dental arch space 14, and also functions as a stop to prevent distal movement or drift of the adjacent upper incisor tooth 49 into the dental arch space 14. The cooperation of the crimpable sleeve 37 and the vertical loop 53 maintains the integrity of the dental arch space 14. This is particularly important in cases demonstrating dental arch length deficiency when the dental arch space 14 was actively gained by means of conventional orthodontic mechanics (such as an open coil spring) prior to the traction of the impacted tooth 12.

The lever arm 28 is bent at elbow 55 to extend into the top of the vertical tube 38 as viewed in FIG. 1, and bent again at elbow 56 adjacent the inner end 57 of the lever arm 28 at the bottom end of the tube 38 to secure the arm 28 inside the vertical tube 38 of connector 34. The arm 28 is affixed to the vertical tube 38 by pinching the lips 39 against the lever arm 28. In this position for the lever arm 28, the intra-oral magnetic unit 18 is on the gingival side of the arch wire 36.

The length of the lever arm 28 from the elbow 55 to the intra-oral magnetic unit 18 sets the desired position for the intra-oral magnetic unit 18 with respect to the intra-boney magnetic unit 16. In the initial traction phase, the intra-oral magnetic unit 18 is placed in close proximity with the oral mucosa along the alveolar line 24 of the gingival side of the arch wire 36 (FIG. 1).

To increase the length of lever arm 28, the bend at elbow 55 would be made at a location closer to inner end 57. Conversely, to decrease the length of lever arm 28, the bend at elbow 55 would be made further from the inner end 57; or, alternatively a loop (not shown) could be formed in the arm 28 between the elbow 55 and the outer end 30 of the lever arm 28.

After the impacted tooth 12 has partially erupted into the oral space 14, the intra-oral magnetic unit 18 should be repositioned from the gingival side of the arch wire 36 to the occlusal side of the arch wire 36, by utilizing the lever arrangement shown in FIG. 2. By lowering the intra-oral magnetic unit 18 as viewed in FIGS. 2 and 3 from adjacent the gingival line to adjacent the occlusal plane, the impacted tooth 12 may be more accurately guided into the dental arch space 14.

The lever arm in FIG. 2 and similar parts thereof which are shown in FIG. 1, are identified by the same numeral and a prime suffix "'". The lever arm 28 is straightened and rebent at elbow 55' so that the arm 28' extends horizontal from the occlusal side of the tube 38 of connector 34 and bent again at elbow 56' adjacent the inner end 57' of the arm 28' at the gingival side of the tube 38, to secure the arm 28' inside the tube 38.

The lever arm 28' can be rotated around its axis (torque) shown by the arrow in FIG. 2, so that an inclination of the magnetic member 32 in the sagittal plane is performed to provide an uprighting effect on the malposed impacted tooth 12.

The lever arm in FIG. 3 and similar parts thereof shown in FIG. 1 are identified by the same numeral and the suffix "a". The positioning of the magnetic member 32 is determined by the location of the magnetic piece 22 implanted in the jaw 13. The length of the lever arm 28a is adjusted to provide the proper three dimensional position for the magnetic member 32. Thus, the distance between the right angled bend at the elbow 58 and the magnetic member 32 provides the desired initial treatment point for the magnetic member 32. The arm 28a is again bent at the elbow 55a at the gingival side of the tube 38 of connector 34 and a third bend is made at the elbow 56a at the occlusal side (bottom) of the tube 38, to secure the arm 28a to the tube 38 of the connector 34. The lever arm 28a would be used for the final phase of the traction process, and would be positioned on the occlusal side of the arch wire 36.

Turning now to FIG. 7, a lower cuspid 60 is shown impacted in the lower jaw 61. The sterile intra-bony magnetic unit 16 is bonded to the tip 62 of the cuspid 60. A flap 64 similar to flap 25 in FIG. 1, is surgically provided and extends from the alveolar ridge 65 and downward therefrom, as viewed in FIG. 7. After spreading the flap 64 some of the bone 66 is removed to provide the pathway 66' for inserting the intra-bony magnetic unit 16 into the lower jaw 61 and bonding to the impacted tooth 60. Closure of the flap 64 hygienically isolates the intra-bony magnetic unit 16 from the non-sterile oral cavity.

A dental arch space 67 is provided between the lower premolar 68 and the lower lateral incisor 69 to receive the impacted tooth 60. A finger spring 70 resiliently contacts the premolar 68 to prevent drift in the mesial direction into the space 67. A finger spring 72 resiliently contacts the lateral incisor 69 to prevent drift in the distal direction into the space 67. The inner ends 73, 74 of springs 70, 72 respectively are attached to a lower removable plate 75 secured to the lingual side of the dental arch. When healing from the surgical procedure is completed the intra-oral magnetic unit 18 is inserted in the dental arch space 67 and magnetically arranged for attracting the intra-bony magnetic unit 16 and simultaneously pulling the impacted cuspid 60 into the space 67. The intra-oral magnetic unit 18 may be secured to the plate 75 or to an upper plate (not shown).

The spring fingers 70 and 72 may also be used to create the arch space 67. The tension from the spring fingers 70, 72 bearing against the premolar 68 and the lower lateral incisor 69 respectively, cause these teeth to spread further apart from each other until deriving the desired dimension for the space 67. Therefore, the spring fingers 70, 72 attached to the plate 75 may function both as a space expander and a space maintainer.

Figure 8:
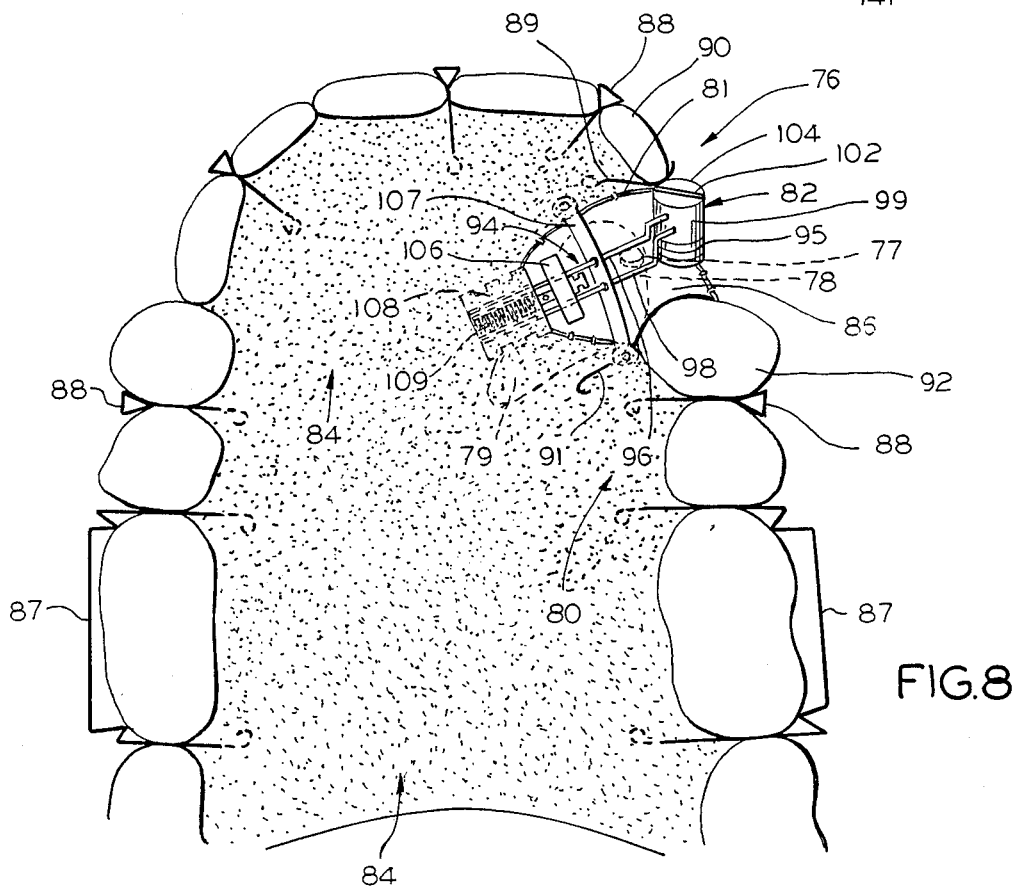
FIG. 8 illustrates a removable hygienic magnetic eruptor and having a horizontal adjustment means and vertical adjustment means for setting the spatial position of the intra-oral magnetic unit with respect to the intra-bony magnetic unit.

Now referring to FIG. 8 of the drawings, a removable upper hygienic magnetic eruptor indicated generally by the reference numeral 76 is illustrated. An intra-bony magnetic unit 77 is bonded to the crown 78 of an upper cuspid 79 impacted in the upper jaw 80.

Similar as in FIGS. 1 and 7, an incision is made to provide a flap 81 to enable some bone removal, and thereafter upon healing from the incision the intra-bony magnetic unit 77 is inserted into the upper jaw 80 for bonding to the impacted tooth 79.

An intra-oral magnetic unit 82 is supported by a removable upper acrylic plate 84 and extends into a dental arch space 86 provided for receiving the impacted cuspid tooth 79.

The plate 84 is supported on the upper dental arch by Adams clasps 87 and triangular clasps 88. A finger spring 89 resiliently contacts the lateral incisor 90 to prevent distal drift into the space 86, and a finger 91 resiliently contacts the premolar 92, to prevent mesial drift into the space 86. The spring fingers 89, 91 may also function to gain or create the dental arch space 86 and then serve to maintain the space 86.

The intra-oral magnetic unit 82 comprises a lever arrangement 94 and an externally threaded magnet 95. The lever arrangement 94 includes a pair of lever arms 96, 98 attached at the outer ends to an internally threaded ring 99, for receiving the magnet 95. A screw driver notch 102 is formed in the top 104 of the magnet 95 for revolving the magnet 95 to adjust the vertical position of the magnet 95.

The lever arms 96, 98 extend through a stabilizer block 106, a stabilizer bar 107 and into a housing 108. A screw 109 upon being rotated moves the block 106 and the lever arms 96, 98 outward (in this case) or inward, and thereby may precisely adjust the lateral position of the magnet 95.

As in the embodiment of FIG. 1, the intra-oral magnetic unit 82 has substantially more magnetic flux than the magnetic unit 77, and this in addition to the rigid attachment of the intra-oral magnetic unit 82 to the removable plate 84 cause movement of the magnetic unit 77 and the impacted tooth toward the intra-oral magnetic unit 82 and into the dental arch space 86.

At the outset of treatment, the intra-oral magnet 95 is adjacent the alveolar ridge of the gum. After the impacted tooth 79 begins to erupt into the space 86, the magnet 95 is threadedly adjusted downward to adjacent the occlusal plane for completing the traction of the impacted tooth 79 into the space 86.

Figure 9:
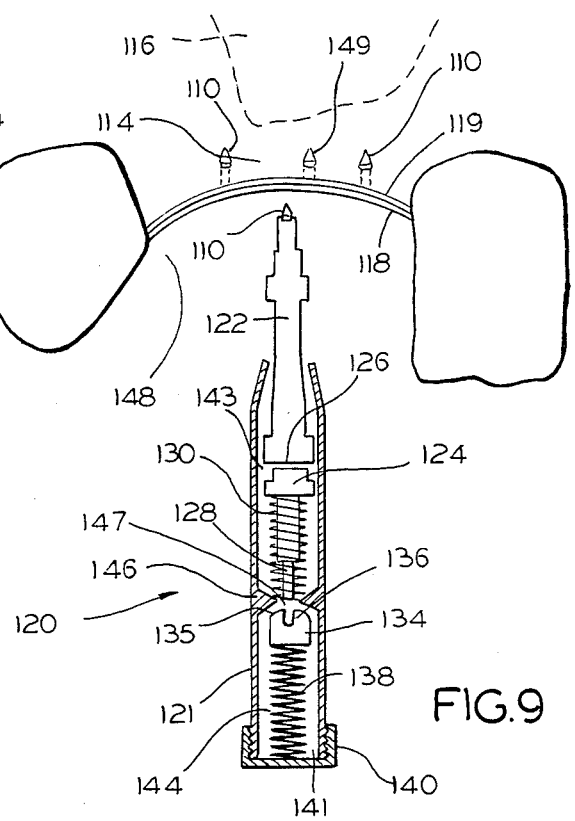
FIG. 9 illustrates a spring impact magnetic particle implanting tool for embedding the intra-bony magnetic particles in the bony plate between the impacted tooth and the oral cavity, thereby applying the indirect magnetic eruption technique, and further showing intra-bony magnetic particles embedded in the bone plate between the impacted tooth and the alveolar ridge.

In FIG. 9, intra-bony magnetic implant particles 110 are inserted in the bony plate 114 between the impacted tooth 116 and the oral mucosa 118/periostium 119. Instead of implanting a plurality of intra-bony magnetic particles 110, a single particle 110 may suffice depending upon the particular case.

The magnetic particles 110 may be implanted by a surgical procedure as aforedescribed or by a non-invasive procedure utilizing a spring impact magnetic particle implanting tool indicated generally by the reference numeral 120.

The magnetic particle implant tool 120 includes a housing 121 containing an impact pointer 122 holding the magnetic particle 110; a hammer plunger 124 having a flat head 126 at the outer end and a projectile pin 128 at the inner end; a light compression coil spring 130 coiled around the hammer plunger 124; a trigger 134 having an outer rim 135 leading into a central opening 136; and an adjustible heavy compression coil spring 138.

A threaded cap 140 closes the rear or inner end 141 of the housing 121. The housing 121 is divided into a forward compartment 143 and a rear compartment 144 by a divider 146 having a central opening 147.

The area to be treated is anasthetized locally, prepped and a small incision is made through the mucosa 118 and the peristeal 119.

The impact tool 120 is loaded by press fitting the magnetic particle 110 in the input pointer 121 and the loaded impact tool 120 is passed through the dental arch space 148 and then inserted in the incision, making close contact with the bony plate 114. By increasing gradually the compression force against the bone 114, the impact pointer 121 recesses inward, forcing the hammer plunger 124 inward for loading (compressing) the light coil spring 130. Concomitantly, the projectile pin 128 of the hammer plunger 124 which is initially off centered, contacts and pushes the trigger 134 back or inward by contacting the outer rim 135 of the trigger 134. This action compresses and thereby loads the heavy coil springs 138. As the heavy coil spring 138 is continuously being loaded, the projectile pin 128 slides from its off-centered position toward the center of the housing 121 until it slips into the central opening 136 of the trigger 134. At this point the tension resisting the heavy compression spring 138 is abruptly dropped, causing the trigger 134, the hammer plunger 124 and the impact pointer 121 to snap forward and forcefully impacting against the bony plate 114 for implanting the magnetic particle 110 into the bony plate 114. The magnetic particle 110 has a sharp outer end 146 for making a clean entry into the bony plate 114.

The amount of impacted force can be adjusted by changing the distance from the trigger 134 to the cap 140.

After the magnetic particles 110 have been implanted in the bony plate 114, an intra-oral magnetic unit such as the intra-oral magnetic unit 18 (FIG. 1) or the intra-oral magnetic unit 82 (FIG. 8) would be positioned in the dental arch space 148 for magnetically attracting with the particles 110. However, the intra-oral magnetic unit (fixed or removable) is introduced into treatment after a sufficient interval of time for healing the incision. This time intermission secures the hygienic function of the appliance.

Turning now to FIG. 6, an alternate embodiment is shown for an intra-oral magnetic unit indicated generally by the reference numeral 150. A lever arm 151 is attached at its outer end 152 to an internally threaded ring 154. An externally threaded cylindrical magnet 156 is received in the ring 154. A screw driver notch 158 is formed at the top 160 of the magnet 156 to enable the vertical position of the magnet 156 to be precisely adjusted for controlling the gap between the intra-bony magnet and the intra-oral magnet.

Various modifications of the invention of a hygienic magnetic eruptor described herein, are within the spirit and scope of the invention, the scope of which is limited solely and defined by the appended claims.

I claim:

1. A method for erupting an impacted tooth fully embedded inside the jaw bone into a dental arch space inside the oral cavity, including the steps of:
   inserting a magnetic piece inside the jaw between the impacted tooth and the gingival line adjacent to the dental arch space; and
   positioning an intra-oral magnetic unit inside said dental arch space, said intra-oral magnetic unit including a magnetic member arranged to magnetically attract with the magnetic magnetic piece for pulling said magnetic piece through the gum and into said dental arch space and thereby causing said impacted tooth to erupt through the gum and into said dental space.

2. The method of claim 1 includes:
   initially positioning said magnetic member adjacent the alveolar ridge inside said dental arch space; and
   positioning said magnetic member adjacent said occlusal plane of the dental arch after said impacted tooth has erupted through the gum and into said dental arch space.

3. The method of claim 1 includes:
   forming a tunnel in the jaw bone from the oral cavity to the tip of the crown of the impacted tooth;
   inserting said magnetic piece inside said tunnel;

bonding said magnetic piece to the tip of the crown of the impacted tooth; and closing said tunnel to isolate said magnetic piece from the oral cavity.

4. The method of claim 3 includes:

forming a flap in said gum proximate to the impacted tooth;

deflecting said flap prior to forming said tunnel; and reconnecting said flap to said gum for isolating said magnetic piece from the oral cavity.

5. The method of claim 4 includes suturing said flap to the said gum when reconnecting said flap for isolating said magnetic piece from the oral cavity.

6. The method of claim 4, includes:

delaying the inserting of said intra-oral magnetic unit inside said dental arch space for a predetermined healing period.

7. The method of claim 1 includes:

implanting said magnetic piece between the impacted tooth and said dental arch space.

8. The method of claim 1 includes:

fixidly attaching the intra-oral magnetic unit inside the oral cavity for pulling the magnetic piece with said impacted tooth through the gum and into the dental arch space.

9. The method of claim 4 wherein said magnetic piece is sterile and said reconnected flap isolates the sterile magnetic piece from the non-sterile oral cavity.

10. The method of claim 1 including:

forcibly impacting the magnetic piece into the bony plate between the impacted tooth and the dental arch space.

11. The method of claim 10 including:

making a small incision in the gum adjacent said dental arch space; and impacting said magnetic piece at the location of said incision.

12. A method for erupting an impacted tooth fully embedded inside the jaw bone into a dental arch space inside the oral cavity, including the steps of:

implanting a plurality of magnetic particles in the bone between the impacted tooth and the dental arch space; and positioning an intra-oral magnetic member inside said dental arch space, for magnetically attracting with the magnetic particles to pull said particles out from said bone and into said dental arch space, to thereby cause said impacted tooth to erupt into said dental arch space.

13. The method of claim 1 further includes:

spatially adjusting the position of the intra-oral magnetic unit to guide the path of eruption of said impacted tooth.

14. The method of claim 13, wherein said spatial adjustment of said intra-oral magnetic unit includes:

horizontally adjusting the intra-oral magnetic unit by altering the mesio-distal and/or bucco-lingual positions thereof.

15. The method of claim 14 includes:

vertically adjusting the position of said intra-oral magnetic unit.

* * * * *